US007128710B1

(12) United States Patent
Cranton et al.

(10) Patent No.: US 7,128,710 B1
(45) Date of Patent: Oct. 31, 2006

(54) DISPOSABLE LARYNGOSCOPE BLADES

(75) Inventors: George D. Cranton, Pinellas Park, FL (US); Barry L. Wall, St. Petersburg, FL (US)

(73) Assignee: Azimuth Corporation, Largo, FL (US)

( * ) Notice: Subject to any disclaimer, the term of this patent is extended or adjusted under 35 U.S.C. 154(b) by 621 days.

(21) Appl. No.: 10/637,032

(22) Filed: Aug. 8, 2003

(51) Int. Cl.
*A61B 1/267* (2006.01)

(52) U.S. Cl. ...................................... 600/199; 600/185

(58) Field of Classification Search ......... 600/185–199
See application file for complete search history.

(56) References Cited

U.S. PATENT DOCUMENTS 2,354,471 A 7/1944 Macintosk
4,273,112 A * 6/1981 Heine et al. ................ 600/193
4,295,465 A 10/1981 Racz et al.
4,406,280 A * 9/1983 Upsher ....................... 600/193
4,705,024 A 11/1987 Bainton
D297,363 S 8/1988 Salerno
4,924,855 A 5/1990 Salerno
4,947,896 A 8/1990 Bartlett
D312,500 S 11/1990 Abadir
5,003,962 A * 4/1991 Choi .......................... 600/190
5,060,633 A * 10/1991 Gibson ....................... 600/193
5,063,907 A 11/1991 Musicant
5,702,351 A * 12/1997 Bar-Or et al. .............. 600/190
5,879,304 A * 3/1999 Shuchman et al. ......... 600/193
D413,977 S 9/1999 Cranton
6,013,026 A * 1/2000 Krauter et al. .............. 600/193
6,036,639 A * 3/2000 Allred et al. ............... 600/193
6,174,281 B1 * 1/2001 Abramowitz ............... 600/196
6,231,505 B1 * 5/2001 Martin ....................... 600/194
6,623,425 B1 * 9/2003 Cartledge et al. ........... 600/195
6,719,688 B1 * 4/2004 Pecherer et al. ............ 600/199
7,044,910 B1 * 5/2006 Cartledge et al. ........... 600/195

* cited by examiner

*Primary Examiner*—Gary L. Welch
*Assistant Examiner*—Henry M Johnson, III
(74) *Attorney, Agent, or Firm*—J. David Haynes

(57) ABSTRACT

A laryngoscopes blade of the disposable variety for use with a Fiber Optic Green System Handle having a blade portion made from stainless steel and a heel portion made from thermoplastic resin.

4 Claims, 3 Drawing Sheets

12
26
32
42
10
18
22
20
14
16
15

10
12
14
15
16
18
20
22
23
24
26
28
32
36
40
42
45
46
47
48
3

10
29
34
35
12
30
40
39
38
36
26
27
31
48

DISPOSABLE LARYNGOSCOPE BLADES

FIELD OF THE INVENTION

This invention relates to Laryngoscope blades generally and more particularly to single use laryngoscopes blades of the disposable variety for use with a Fiber Optic Green System Handle.

DESCRIPTION OF THE PRIOR ART

Laryngoscope blades of the Green System type are used to examine and visualize a patients upper airway and aid in the placement of a tracheal tube during intubations, and also during resuscitations. Multiple use or reusable laryngoscope blades are well known in the industry but present at least a two fold problem, namely: 1) studies have shown that as many as sixteen percent of the laryngoscope blades that had been cleaned were still contaminated and 2) re-cleaning reusable blades can currently cost from $3.25–$5.00 depending on geographic labor costs. Prior art disposable laryngoscope blades have not been well received in hospitals in the United States as they all are constructed primarily from plastic and tend to twist and flex during use and some have even broken in use.

SUMMARY OF THE INVENTION

The object of this invention was to develop a disposable single use laryngoscope blade for use in a handle-blade world-wide system in conjunction with a Fiber Optic Green System Handle that would be acceptable for every surgical procedure and everyday usage in the hospital, as well as in the field, and at a price that was cost effective. To that end, a device that is the subject of this invention achieves the following: 1) a stainless steel blade that won't flex or break during use; 2) has traditional profiles and sizes and therefore suitable for use on all patients; 3) cost effective to the hospital when compared to cleaning costs; 4) sterile with no more cleaning or contamination problems. To that end, the blade spatulas are made from type 304 austenitic stainless steel in accordance with the ISO/DIS 7153/3, standard recommended by ASTM (American society for testing metals) which is highly recommended for surgical/medical instruments. The ball plungers which acts as a locking aid, and their springs and covers are also made from type 304 stainless steel. The heel of the blade (also referred to as the foot of the blade) is made from Dupont's Delrin (R) 900P NC 010, a low viscosity acetal resin, a thermoplastic polymer material which is a resin for molding in multi cavity molds and thin sections that are difficult to fill, has good chemical resistance to some alkalies and some acids, has improved thermal stability and is stable during the Gamma sterilization process. To insure that the device is not reused in a hospital environment where sterilization is normally performed by steam autoclaving, the resin material selected will not accept steam autoclaving. The light carrier is made from cast acrylic rods cut and bent in the desired shape and acts as a light carrier from the lamp in the handle to the distal tip of the blade for visualization of the larynx during intubation, while the light carrier fastener is made from polypropylene material and is immune to stress cracking. These disposable blades are used to examine and visualize a patients upper airway and aid in placement of a tracheal tube during intubations. The conventional Fiber Optic Green System handle suitable for use with this blade is mechanically attached to the blade in the conventional manner and light is transmitted from a source in the handle to the distal tip of the blade through the light carrying rod.

In accordance with IAEA (International Atomic Energy Agency) recommended standards, these blades, after the final manufacturing steps have been completed, are packed in sterilized pouches made from material which is stable during gamma ray sterilization, such as Tyvec, and sterilized by gamma ray sterilization processing.

DETAILED DESCRIPTION OF THE PREFERRED EMBODIMENT

Figures 1, 2, 3:
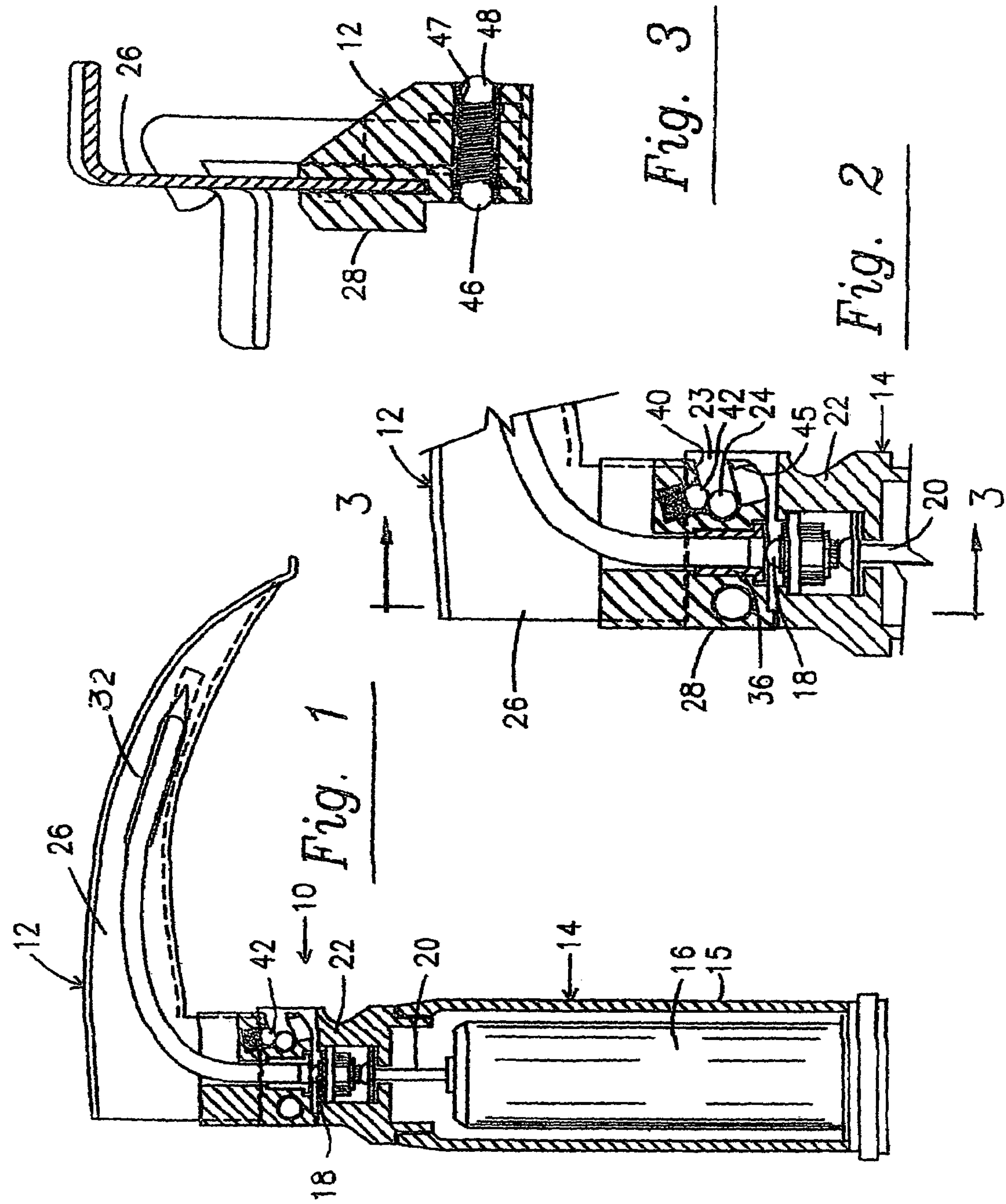
FIG. 1 is a side elevational view of a laryngoscope blade mounted on its cooperating handle with the handle and the heel of the blade shown in section.
FIG. 2 is an enlarged fragmentary view of a portion of the device shown in FIG. 1.
FIG. 3 is a sectional view taken along the lines 3—3 in FIG. 2.
Figure 6:
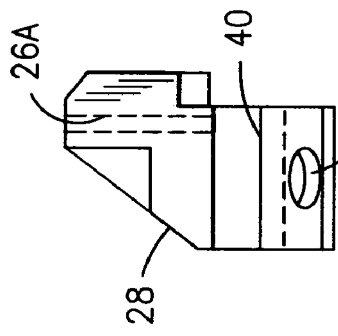
FIG. 6 is a right side view of the heel portion shown in FIG. 4.
Figure 9:
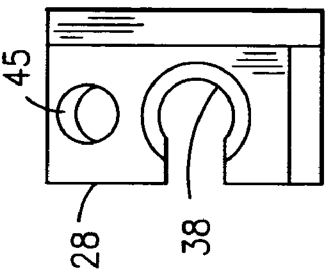
FIG. 9 is a bottom view of the heel portion shown in FIG. 4.
Figure 5:
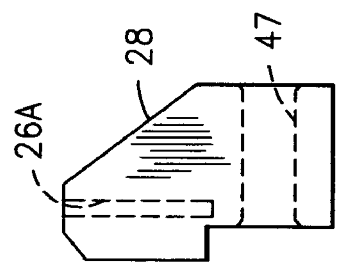
FIG. 5 is a left side view of the heel portion shown in FIG. 4.
Figure 8:
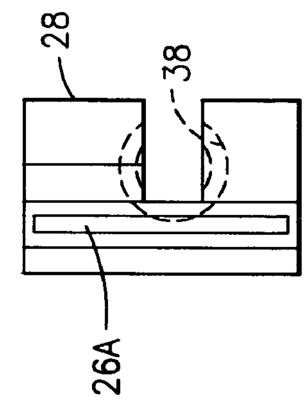
FIG. 8 is a bottom view of the heel portion shown in FIG. 4.
Figure 4:
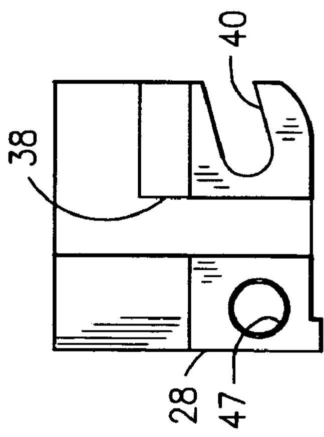
FIG. 4 is a side elevational view of the plastic part of the heel portion of the device of FIG. 1
Figure 7:
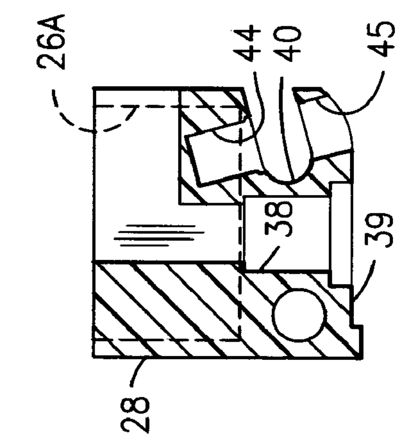
FIG. 7 is a cross sectional view of the heel portion shown in FIG. 4.

Referring now to the drawings a laryngoscope blade-handle assembly is shown generally at 10 and includes a blade portion 12 and a handle portion 14. The handle is of the conventional type referred to as a Fiber Optic Green System Handle which is reusable and includes a gripable housing 15 in which is a source of electrical power in the form of a battery 16, a source of light in the form of a bulb 18 actuated upon its depression and contact with a conductor 20 and a securable mounting end 22 at the upper end thereof surrounding the bulb 18. The mounting end 22 has a slot 23 formed therein traversed by a cross pin 24 and a pair of laterally spaced and opposed detents (not shown), one on each lateral side of the slot 23.

Figure 10:
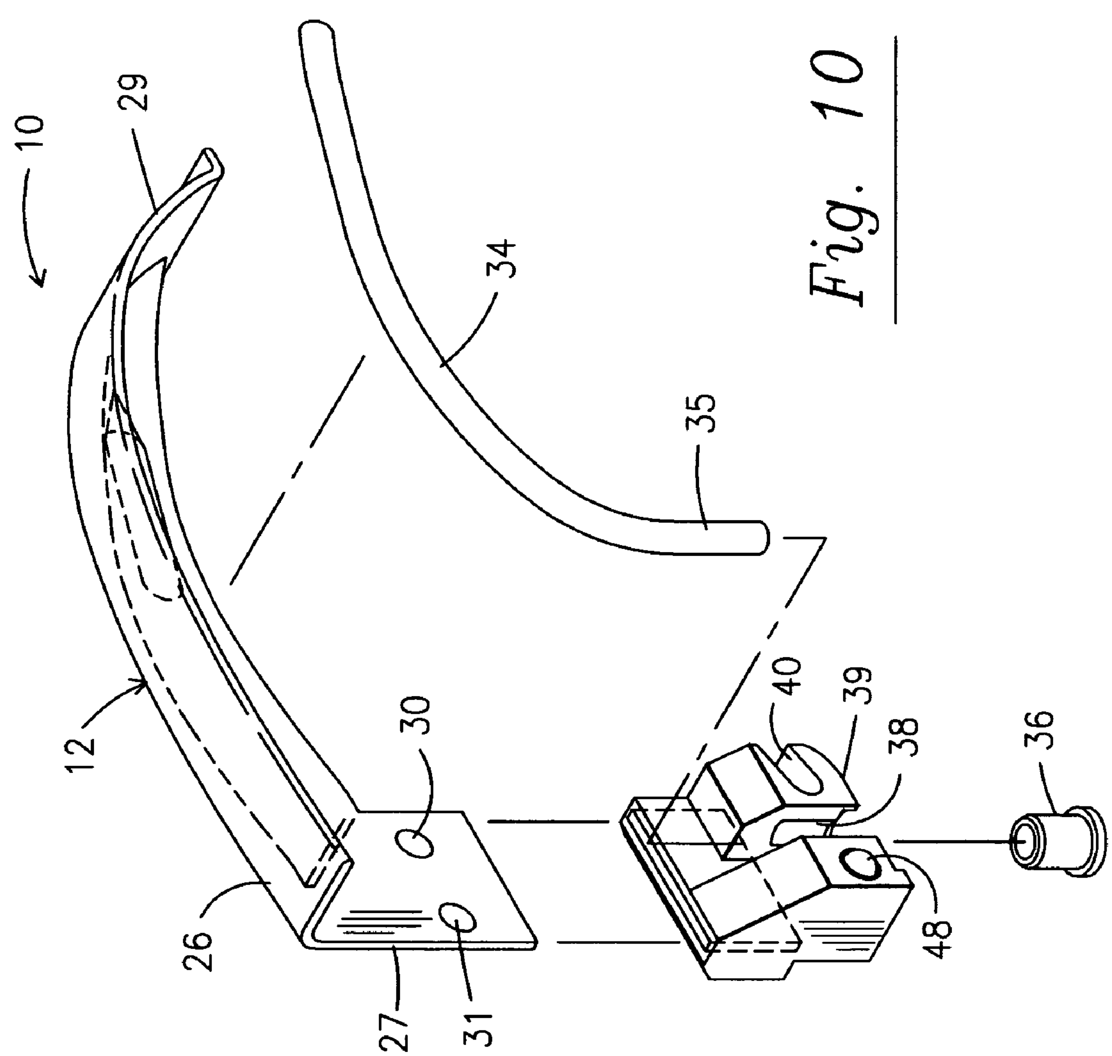
FIG. 10 is an exploded view of the blade portion of the assembly shown in FIG. 1.

The blade portion 12 includes a conventionally flanged blade 26 and a heel portion 28. The blade 26 is made from type 304 austenitic stainless steel and, with reference to FIG. 10, has an attaching proximal end 27, a distal end 29, a pair of securing cross holes 30 and 31 formed laterally in the attaching end 27 and an elongated opening 32 formed intermediate the opposed ends of the blade 26. The opening 32 is formed so as to snugly receive an acrylic light carrier 34 having an elongated rod shape in the conventional light carrier configuration. The light carrier 34 is bent to fit and extends from the distal end 29 of the blade 26 to the bottom 39 of the heel portion 28 and its proximal end 35 at the heel end is bent downwardly and extends into an annular polypropylene fastener 36 and fittingly and securely received therein. The fastener, in turn, is securely received in a vertically extending slot-like opening 38 formed in the side of the heel portion 28 and extending from the bottom 39 to the top of the heel portion so that the carrier 34 extends from the bottom 39 of the heel portion to the distal end 29 of the blade 26.

The heel portion 28 has an inclined slot 40 formed laterally across the right end thereof, which slot receives the cross pin 24 of the handle 14 when assembled thereon. A spring loaded poppet 42 received in an opening 44, formed in the heel portion 28 and open to the slot 40, which poppet resiliently engages the top of the cross pin 24 to assist in holding the assembly together. A hole 45 is formed in the lower part of slot 40 which is slightly larger than the hole 44, to provide access for the spring loaded poppet 42 so that it can be inserted therethrough and into the opening 44. A pair of spring loaded poppets 46 and 48, carried by the heel portion 28 in a cross hole 47, and extending in lateral opposition to engage mating detents (not shown) in the slot 23 of the mating end 22 of the handle 14 to resiliently assist in holding the assembly together. The poppets 42, 46 and 48, along with their springs and mounting sleeves are made from the same type 304 stainless steel as the blade.

The blade 26 of the blade portion 12 can be made from sheet stock material which is first sheared to size, blanked and bent, and holes drilled for molding of the blade 26 of the blade portion 12 can be precision cast out of type 304 austenitic steel and requires no machining. After forming the blade 26, it is merely polished, ultrasonically cleaned and then sand blasted before the heel is molded thereon in an insert molding process in which low viscosity acetal resin plastic, such as Delrin®) 900P, flows into the holes 30 and 31 in the blade 26 to thus form a blade portion assembly which will not separate; the blade 26 being securely and fittingly received in a space 26A in the heel portion, shown in FIGS. 5, 6, 7 and 8 which space is formed intimately around the blade during the molding process. After molding, the heel portion 28 is merely deburred, the light carrier installed, the poppets 42, 46 and 48, along with their springs and stainless steel mounting devices are installed in the heel portion, the blade portion wrapped and then sterilized by gamma ray sterilization to complete the manufacturing process.

The blade portions 12 are contemplated to be supplied in the well known conventional sizes of Macintosh: sizes 2, 3 and 4; Miller: sizes 0, 1, 2, and 3; and special types of pediatric blades.

While only a single embodiment of this invention has been shown and described, it is apparent that changes can be made therein without departing from the scope of this invention as claimed in the following claims.

What is claimed is:

1. A disposable laryngoscope blade compatible with Fiber Optic Green System Handles comprising a blade portion and a heel portion intimately secured thereto and having a proximal mounting end and an acrylic light carrying rod, wherein said blade portion, having a distal and a proximal end, is formed from a type 304 stainless steel, said blade portion after forming has been subjected to the steps of drilling a plurality of holes adjacent its proximal end for molding, then polishing, then ultrasonic cleaning, and then sand blasting, after which said heel portion, which is made from a thermoplastic plastic material that can be sterilized by gamma radiation and cannot be sterilized by steam autoclaving and which is a low viscosity resin suitable for molding in multi-cavity molds and thin sections that are difficult to fill, is intimately molded in a cavity mold upon the proximal end of said blade portion and into said holes in said blade portion, thereafter said heel portion is deburred, and said acrylic light carrying rod is assembled with said blade portion and said heel portion and extends from the distal end of said blade portion to the proximal end of said heel portion.

2. A disposable blade according to claim 1 wherein said heel portion is made from a low viscosity thermoplastic acetal resin.

3. A disposable blade according to claim 2 wherein said resin is Defrin®) 900P.

4. A disposable laryngoscope blade compatible with Fiber Optic Green System Handles comprising: a blade, a heel having a proximal mounting end and a slot therethrough and a mounting means in said slot, and an acrylic light carrying rod, wherein said blade has a distal end and a proximal end with said proximal end being its mounting end, wherein said heel is intimately secured to said proximal end of said blade and wherein said rod is mounted in said heel and extends along said blade and terminates at said distal end of said blade, and wherein said heel is formed from a low viscosity acetal resin capable of being sterilized by gamma radiation while not being subject to sterilization by steam autoclaving; wherein said mounting means is an annular component made from a polypropylene material which securely receives said sod therein and in turn is securely fitted in said slot in said heel portion.

* * * * *